(12) United States Patent
Siebke

(10) Patent No.: US 9,958,020 B2
(45) Date of Patent: May 1, 2018

(54) DISC BRAKE HAVING A CLEARANCE-MONITORING DEVICE, AND METHOD FOR MONITORING CLEARANCE

(71) Applicant: KNORR-BREMSE Systeme fuer Nutzfahrzeuge GmbH, Munich (DE)

(72) Inventor: Alf Siebke, Schondorf am Ammersee (DE)

(73) Assignee: KNORR-BREMSE Systeme fuer Nutzfahrzeuge GmbH, Munich (DE)

( * ) Notice: Subject to any disclaimer, the term of this patent is extended or adjusted under 35 U.S.C. 154(b) by 0 days. days.

(21) Appl. No.: 14/807,972

(22) Filed: Jul. 24, 2015

(65) Prior Publication Data

US 2015/0330470 A1 Nov. 19, 2015

Related U.S. Application Data

(63) Continuation of application No. PCT/EP2014/051401, filed on Jan. 24, 2014.

(30) Foreign Application Priority Data

Jan. 25, 2013 (DE) .......................... 10 2013 100 786

(51) Int. Cl.
*F16D 55/2255* (2006.01)
*F16D 65/56* (2006.01)
(Continued)

(52) U.S. Cl.
CPC ....... *F16D 55/2255* (2013.01); *F16D 55/225* (2013.01); *F16D 65/568* (2013.01);
(Continued)

(58) Field of Classification Search
CPC ............... F16D 66/00; F16D 2066/003; F16D 2066/006; F16D 66/021–66/027
See application file for complete search history.

(56) References Cited

U.S. PATENT DOCUMENTS

| 4,937,554 A * | 6/1990 | Herman | B60Q 1/44 188/1.11 L |
| 5,079,947 A * | 1/1992 | Feldmann | B60T 17/22 340/453 |

(Continued)

FOREIGN PATENT DOCUMENTS

| DE | 40 17 950 A1 | 12/1991 |
| DE | 197 29 024 C1 | 1/1999 |

(Continued)

OTHER PUBLICATIONS

International Preliminary Report on Patentability (PCT/IB/373) issued in PCT Application No. PCT/EP2014/051401 dated Jul. 28, 2015, including Written Opinion (PCT/ISA/237) with English translation (ten (10) pages).

(Continued)

*Primary Examiner* — Thomas J Williams
*Assistant Examiner* — James K Hsiao
(74) *Attorney, Agent, or Firm* — Crowell & Moring LLP

(57) ABSTRACT

A disc brake, in particular for a motor vehicle, includes a brake-application device having a brake lever. An adjustment device, which is coupled to the brake-application device, in particular to the brake lever, is provided in order to adjust for the wear of brake pads and a brake disc. A wear sensor detects a wear value of brake pads and the brake disc. A brake control unit controls the disc brake. The disc brake has a clearance-monitoring device having a control device, which is connected to the wear sensor and the brake control unit. A corresponding method for monitoring a clearance of a disc brake is provided.

16 Claims, 6 Drawing Sheets

(51) Int. Cl.
  *F16D 55/225* (2006.01)
  *G01N 3/56* (2006.01)
  *F16D 66/02* (2006.01)
  *F16D 66/00* (2006.01)

(52) U.S. Cl.
  CPC ............. *F16D 66/027* (2013.01); *G01N 3/56* (2013.01); *F16D 2066/001* (2013.01); *F16D 2066/003* (2013.01); *F16D 2066/006* (2013.01)

(56) References Cited

U.S. PATENT DOCUMENTS

| | | | |
|---|---|---|---|
| 5,207,299 A | 5/1993 | Feldmann | |
| 5,339,069 A * | 8/1994 | Penner | B60T 17/22 116/208 |
| 5,848,673 A * | 12/1998 | Strauss | F16D 65/568 188/1.11 L |
| 6,105,730 A * | 8/2000 | Ekeroth | F16D 65/60 188/1.11 L |
| 6,129,183 A * | 10/2000 | Ward | F16D 65/183 188/1.11 L |
| 6,250,434 B1 | 6/2001 | Baumgartner et al. | |
| 6,581,728 B2 * | 6/2003 | Borugian | F16D 51/20 188/1.11 E |
| 6,626,269 B2 * | 9/2003 | Shaw | F16D 65/18 188/196 V |
| 6,774,595 B1 | 8/2004 | Laxhuber et al. | |
| 6,820,730 B2 * | 11/2004 | Angerfors | F16D 65/568 188/71.9 |
| 7,244,003 B2 * | 7/2007 | Larson | B60T 8/00 188/1.11 L |
| 7,322,447 B2 * | 1/2008 | Deckhut | F16D 65/18 188/1.11 L |
| 7,413,061 B2 | 8/2008 | Wagner et al. | |
| 7,600,455 B2 * | 10/2009 | Gass | B23D 59/001 83/477.1 |
| 7,926,626 B2 | 4/2011 | Iraschko | |
| 8,752,422 B2 | 6/2014 | Helf | |
| 9,168,905 B2 * | 10/2015 | Welin | F16D 66/027 |
| 2002/0126007 A1 * | 9/2002 | Weant | B60Q 1/44 340/479 |
| 2003/0024773 A1 * | 2/2003 | Goncalves | F16D 66/00 188/1.11 E |
| 2003/0084714 A1 * | 5/2003 | Chang | G01L 5/28 73/121 |
| 2005/0212357 A1 * | 9/2005 | Adams | B60T 17/18 303/122.03 |
| 2005/0241894 A1 * | 11/2005 | Baumgartner | F16D 65/567 188/79.51 |
| 2006/0149440 A1 * | 7/2006 | Pettersson | B60T 17/221 701/34.4 |
| 2011/0241866 A1 * | 10/2011 | Todd | B60T 17/088 340/453 |
| 2011/0254679 A1 * | 10/2011 | Todd | B60T 17/221 340/454 |

FOREIGN PATENT DOCUMENTS

| | | |
|---|---|---|
| DE | 197 31 696 A1 | 2/1999 |
| DE | 199 33 962 C2 | 1/2003 |
| DE | 101 38 452 A1 | 2/2003 |
| DE | 10 2004 037 771 A1 | 3/2006 |
| EP | 0 421 066 A1 | 4/1991 |
| EP | 0 567 155 A1 | 10/1993 |
| EP | 0 567 155 B1 | 3/1996 |
| EP | 2 520 817 A1 | 11/2012 |
| GB | 2 332 027 A | 6/1999 |
| JP | 2000-234641 A | 8/2000 |
| JP | 2003-4075 A | 1/2003 |
| JP | 2005-527420 A | 9/2005 |
| WO | WO 2012/013702 A2 | 2/2012 |

OTHER PUBLICATIONS

International Search Report (PCT/ISA/210) dated Jul. 18, 2014, with English translation (four (4) pages).
German Office Action dated Jun. 30, 2014 (nine (9) pages).
Japanese-language Office Action issued in counterpart Japanese Application No. 2015-554157 dated Jan. 9, 2018 with English translation (20 pages).

\* cited by examiner

DISC BRAKE HAVING A CLEARANCE-MONITORING DEVICE, AND METHOD FOR MONITORING CLEARANCE

CROSS REFERENCE TO RELATED APPLICATIONS

This application is a continuation of PCT International Application No. PCT/EP2014/051401, filed Jan. 24, 2014, which claims priority under 35 U.S.C. § 119 from German Patent Application No. 10 2013 100 786.4, filed Jan. 25, 2013, the entire disclosures of which are herein expressly incorporated by reference.

BACKGROUND AND SUMMARY OF THE INVENTION

The invention relates to a disc brake, in particular for a motor vehicle, having a clearance monitoring device. The invention also relates to a method for monitoring the clearance of a disc brake.

Such disc brakes are known in various designs. For their safe and reliable functioning it is necessary that a defined distance, referred to as the clearance, is maintained between their friction partners (brake pads and brake disc), under all operating conditions.

Wear adjustment devices are known in different designs, for example mechanical adjusters which ensure there is constant clearance within certain limits in the pneumatically acting disc brakes which are customary nowadays in heavy commercial vehicles. In this context, whenever the brakes are activated the adjustment device is actuated, for example, by means of a positioning element of a brake application device of the disc brake. In the case of wear of brake pads and the brake disc, automatic adjustment of the pads takes place by means of the adjustment device, for example by means of an adjustment movement of pressure rams with variable length.

A structural predefined clearance is formed as fixed geometric variables in the components which are involved in the adjustment process. Continuous monitoring of the clearance is not possible owing to the purely mechanical conditions or because of a lack of sensors. Therefore, nowadays only manual measurement of the clearance, to be performed within the scope of the regular brake inspection, is provided. However, this checking takes place, of course, only at relatively long time intervals or mileage or kilometerage intervals, for example when changing brake pads and, furthermore, only in the cold state of the disc brake. Therefore, the clearance remains unobserved over long driving distances and during different operating states of the disc brake, and any critical changes remain undetected.

Disc brake designs are known which permit the clearance to be monitored and, moreover, even permit it to be set actively or corrected during operation. For example, this is carried out in a pneumatically activated disc brake in that the adjustment device is driven electrically, and therefore the brake pads are moved relative to the brake disc. A corresponding control logic uses operating parameters of the electric drive to measure the clearance which is present and, if appropriate, set a desired clearance. DE 19731696 A1 illustrates an example of this.

However, such designs have previously not been commercially successful due to the considerable technical development leap as well as the associated costs.

A further type of brake which can permit monitoring of clearance is known in the form of an electromechanical disc brake. The brake mechanism is activated here purely electrically, and monitoring and setting of the clearance can be carried out with the control electronics which are necessary for braking However, this design constitutes an even greater technological step, and the use of such systems in commercial vehicles on a standard basis can not be anticipated. An example of this is illustrated by document DE 19933962 C2.

Therefore, the object of the present invention is to improve a disc brake, in particular a pneumatic disc brake, of a conventional design with clearance monitoring and with the smallest possible structural expenditure and expense.

A further object is to provide an improved method for monitoring clearance.

These and other objects are achieved by way of a disc brake, and corresponding method, in accordance with embodiments of the invention.

A basic concept of the invention is that a clearance monitoring device is provided with a control device which is connected to the wear sensor and to the brake control unit. An already existing wear sensor, which is frequently used in disc brakes, is therefore used.

A disc brake according to the invention, in particular for a motor vehicle, comprises a brake-application device, in particular one having a brake lever, an adjustment device which is coupled to the brake application device, in particular to the brake lever, in order to adjust the wear of brake pads and of a brake disc, a wear sensor for detecting a wear value of the brake pads and the brake disc, and a brake control unit. The disc brake has a clearance monitoring device with a control device which is connected to the wear sensor and to the brake control unit.

This provides the advantage that a disc brake with a clearance monitoring device is provided with the smallest possible expenditure.

A method according to the invention for monitoring clearance of such a disc brake comprises the acts of: forming current value pairs from current brake pressure values and detected current signal values of the wear sensor during a braking process; comparing the formed current value pairs with previously stored reference values; and evaluating the comparison and outputting of messages in order to monitor the clearance.

It is therefore advantageously possible to detect and display or report unacceptable deviations from defined or previously specified clearance values.

In one embodiment, the control device of the clearance monitoring device is designed to detect a current signal value of the wear sensor with a detection unit. The detection unit can detect a change in the current signal value of the wear sensor over time. This is particularly advantageous when the wear sensor is adjusted. A change can therefore be detected immediately.

A further embodiment provides that the control device of the clearance monitoring device is provided for forming current value pairs from current brake pressure values and detected current signal values of the wear sensor and for comparing the current value pairs with stored reference values with a comparator unit. The reference values can be, for example, pressure travel characteristic curves of a brake cylinder of the associated disc brake. It is particularly advantageous if these pressure travel characteristic curves can be learned in the new state, which permits a different embodiment.

The current brake pressure values can therefore originate from the brake control unit and/or can be output values of at least one other sensor. The brake control unit can have corresponding table values and/or characteristic curve values. Of course, an existing pressure sensor or else force sensor can also be used as well. The stored reference values are also stored in the brake control unit.

Furthermore, the stored reference values can be stored in a memory unit of the control device. It is advantageous here if these are the learned characteristic curve values and further learned values, since greater precision is then possible.

In yet a further embodiment, the control device of the clearance monitoring device has an evaluation unit for evaluating the results of the comparator unit. In this way, the detected values can be differentiated on the basis of trends and secondary conditions. Warnings and displays can be effected precisely in this respect.

In addition, there is provision that the clearance monitoring device comprises a signaling unit which signals messages about the state of the clearance monitoring acoustically, visually, haptically and/or alphanumerically on the basis of the evaluation of the evaluation unit. A driver of the vehicle can therefore be alerted early enough to problems or compliance with maintenance periods or the need to look for a workshop. Furthermore, the messages can be stored and can be retrievable by maintenance personnel.

In order to include secondary conditions and to estimate trends and detected measured values, the clearance monitoring device can also have at least one temperature detector. In this context, already existing temperature sensors or else additional ones can be used.

The control device of the clearance monitoring device can be a component of the brake control unit, as a result of which no significant additional space requirement results for the disc brake.

In the method step of forming current value pairs (p/V), the current brake pressure values are supplied by the brake control unit and/or an additional sensor. The brake pressure values are already present in the brake control unit, and therefore no additional sensors requiring space have to be installed.

In one embodiment there is provision that in the method step of evaluating, a previously definable nominal clearance without adjustment is detected if a current value pair corresponds to a stored value pair which is assigned to a correct clearance, and the following value pair does not have any change in the detected current signal value of the wear sensor but does have a strong rise in the brake pressure. In this way, simple differentiation of the further cases is possible.

In this context, in the method step of evaluating, previously definable nominal clearance, enlarged owing to wear, with adjustment is detected if a current value pair corresponds to a stored value pair which is assigned to a correct clearance, and the following value pair has a change in the detected current signal value of the wear sensor but does not have a strong rise in the brake pressure.

And for a further case, in the method step of evaluating, a previously definable nominal clearance is detected as being undershot if the brake pressure of a current value pair is lower than the brake pressure which is assigned to a previously definable, correct clearance, and the subsequent value pair does not have any change in the detected current signal value of the wear sensor but does have a strong rise in the brake pressure or has a change in the detected current signal value of the wear sensor but does not have a strong rise in the brake pressure.

In this way, differentiation between cases can advantageously be performed on the basis of the value pairs, in order to monitor the clearance.

Furthermore, in the method step of evaluating, thermal influences are also included by means of a temperature detector, as a result of which the reliability of the messages is increased.

A further increase in the reliability is achieved in that in the method step of evaluating, a warning or a warning signal is not output until after a specific number of braking operations.

An increase in the reliability is also possible with previously carried out learning of the reference values in the brake control unit and/or the memory unit.

Furthermore, in a further embodiment it is advantageously permitted that a friction point can be detected in that the current value pairs are compared with stored value pairs if a current value pair of the current value pairs which are compared with stored value pairs has a strong rise in the brake pressure.

With the clearance monitoring device according to the invention and the corresponding method according to the invention for monitoring clearance, the current clearance can be detected and monitored continuously or sufficiently frequently.

Differentiated detection of enlarged correct and undershot clearance is possible.

The clearance can be monitored and detected specifically for each brake.

The expenditure for this is minimized in that no additional space is necessary and output values of existing functional units continue to be used.

Additional sensors on the wheel brake for detecting the clearance or clearance gap are not necessary. The associated separate electronic evaluation units (setpoint/actual value comparison) and output units can be dispensed with.

Other objects, advantages and novel features of the present invention will become apparent from the following detailed description of one or more preferred embodiments when considered in conjunction with the accompanying drawings.

DETAILED DESCRIPTION OF THE DRAWINGS

Figure 1:
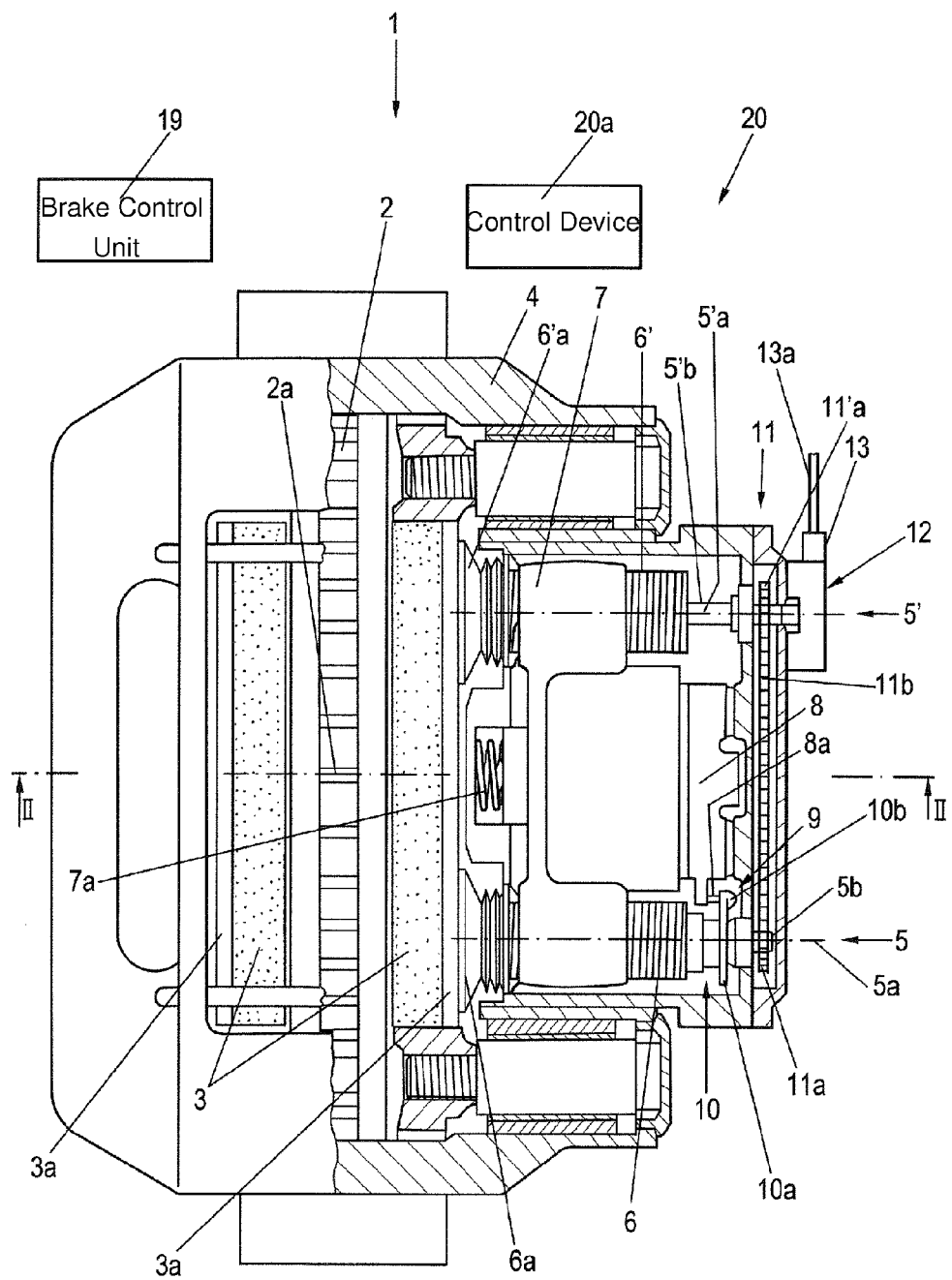
FIG. 1 shows a schematic partial-sectional view of an exemplary embodiment of a disc brake according to the invention with a clearance-monitoring device.
Figure 2:
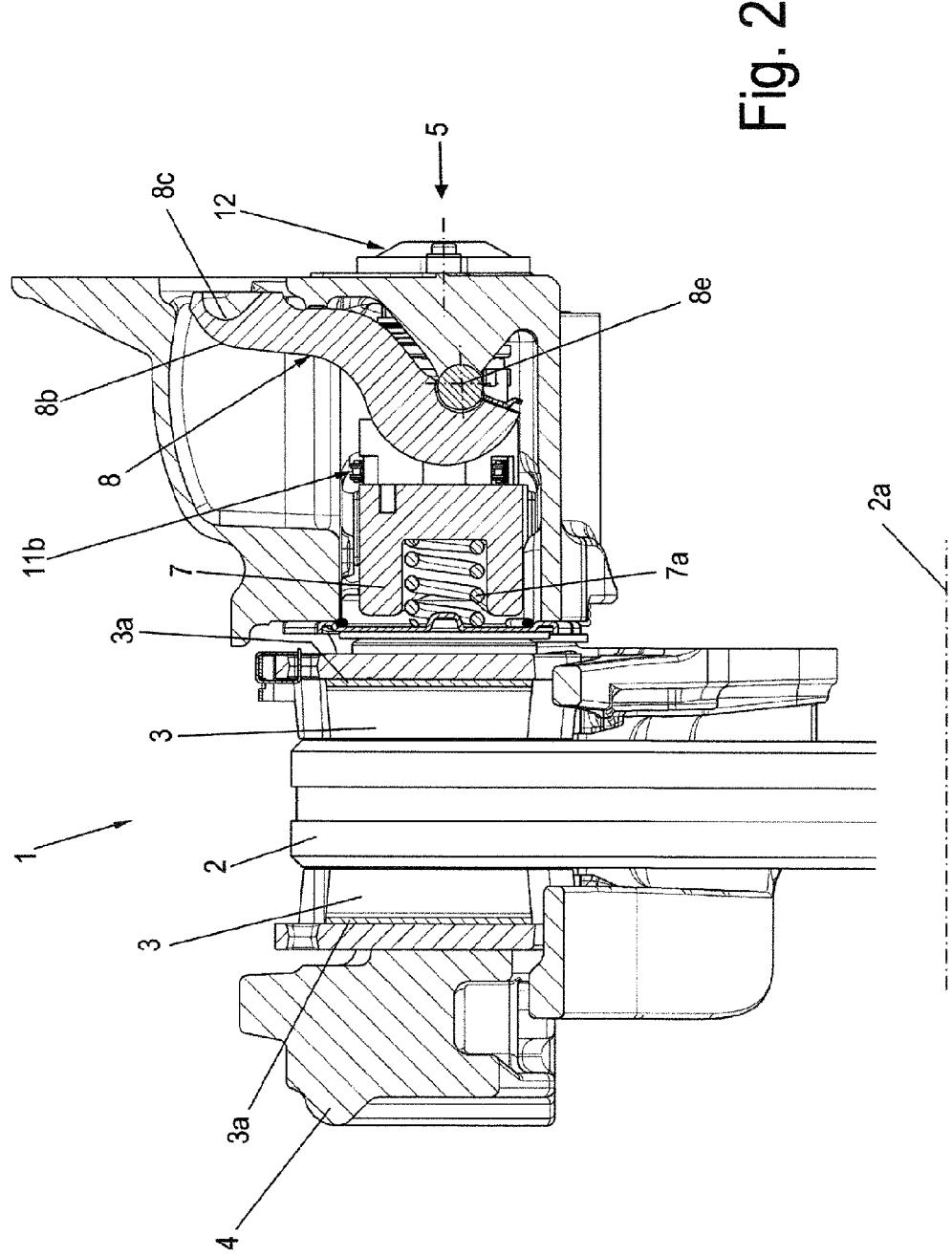
FIG. 2 shows a schematic sectional-view of the exemplary embodiment along the line II-II according to FIG. 1 in a variant.

FIG. 1 shows a schematic partial-sectional view of an exemplary embodiment of a disc brake 1 according to the invention with a clearance-monitoring device 20. FIG. 2 illustrates a schematic sectional view of the exemplary embodiment along the line II-II according to FIG. 1 in a variant.

The disc brake 1 has a brake disc 2 with a brake disc axis 2a. A brake caliper 4, embodied here as a floating caliper, engages over the brake disc 2. A brake pad 3, in each case with a brake pad carrier 3a, is arranged on each side of the brake disc 2. The brake pad 3, which is located on the left-hand side of the brake disc 2 in FIGS. 1 and 2 is referred to as the reaction-side brake pad 3, and the brake pad 3 which is arranged on the right-hand side of the brake disc 2 is referred to as the brake-application-side brake pad 3.

In this exemplary embodiment, the disc brake 1 is embodied as a two-ram brake with two spindle units 5 and 5'. Each spindle unit 5, 5' has a threaded ram 6, 6' which is embodied as a hollow shaft with an external thread. An adjustment device 10, about which further details are given below, is inserted in the threaded ram 6 of the one spindle unit 5. One axis of this spindle unit 5 is therefore referred to as an adjuster axis 5a. The adjustment device 10 is provided with an adjuster shaft 5b which interacts in a rotationally fixed fashion with the threaded ram 6.

The other spindle unit 5' has an axis which is referred to as a driver axis 5', and a driver shaft 5'b which is inserted in the threaded ram 6' of the other spindle unit 5' and is connected in a rotationally fixed fashion to the threaded ram 6'.

The brake-application-side brake pad carrier 3a is connected to the spindle units 5, 5' via pressure elements 6a, 6'a which are arranged at the ends of the threaded rams 6, 6'. The other, reaction-side brake pad carrier 3a is secured to the other side of the brake disc in the brake caliper 4. The threaded rams 6, 6' are each rotatably arranged in a crossmember 7, which is also referred to as a bridge, with their external threads in threaded bores of the crossmember 7. The thread is embodied here with a gradient in the self-locking region. As a result of the rotational movement of the threaded rams 6, 6' in the crossmember 7, the axial position of the threaded rams 6, 6' relative to the crossmember 7 changes. The term axial position means here a position of the threaded rams 6, 6' in the axial direction of the brake disc axis 2a and of the axes 5a, 5'a. The axes 5a, 5'a run parallel to the brake disc axis 2a here.

The crossmember 7 and the threaded rams 6, 6' can be activated by a brake-application device, here a brake lever 8 with a pivoting axis 8e (see FIG. 2) at a right angle to the brake disc axis 2a of the brake disc 2. The brake lever 8 has a lever body 8d which interacts with the crossmember 7 via bearing sections.

The crossmember 7 can be adjusted in the direction of the brake disc axis 2a by the brake lever 8. A movement toward the brake disc 2 is referred to as a brake-application movement, and a movement in the opposite direction is referred to as a release movement. A return spring 7a, not explained further, is accommodated in the center of the crossmember 7 in a corresponding recess on the pad-side end of the crossmember 7, and is supported on the brake caliper 4. During the release movement, the crossmember 7 is adjusted into the released position (shown in FIG. 1 and FIG. 2) of the disc brake 1 by way of the return spring 7a.

A distance between the brake pads 3 and the brake disc 2 in the released position is referred to as clearance. This clearance becomes larger owing to pad wear and disc wear. If this is not compensated, the disc brake 1 cannot achieve its peak performance, since an activation stroke of the activation mechanism, i.e. here the activation stroke or a pivoting angle of the brake lever 8, is enlarged.

The disc brake 1 can have different force drives. The brake lever 8 is, for example, activated pneumatically here. For this purpose, the brake lever 8 has an arm 8b which is connected to the lever body 8d (FIG. 2). Arranged at the free end of the arm 8b is a force-application section 8c which interacts with a force source, for example a pneumatic cylinder. With respect to the design and function of a pneumatic disc brake 1, reference is made to the corresponding description of DE 197 29 024 C1.

The adjustment device 10 is designed to adjust the wear of a previously defined clearance, which is referred to as nominal clearance. The term "adjustment" is to be understood as meaning a reduction in the clearance. The previously defined clearance is determined by the geometry of the disc brake 1 and has what is referred to as structural clearance. In other words, the adjustment device 10 reduces clearance which is present if this clearance is too large with respect to the previously defined clearance.

The adjustment device 10 is arranged on the one spindle unit 5, coaxially with respect thereto, and with respect to its threaded ram 6 and the adjuster axis 5a. The components and functional groups of the adjustment device 10, which is described in detail in, for example, document DE 10 2004 037 771 A1, is arranged in the axial direction about the adjuster shaft 5b and therefore in the direction of the adjuster axis 5a. The adjustment device 10 is mounted with its brake-application-side end in the brake caliper 4 in a way which is not explained in more detail. In this respect, reference is made to document DE 10 2004 037 771 A1. At the brake-application-side end of the adjuster shaft 5b, a synchronization wheel 11a of a synchronization device 11 is attached in a rotationally fixed fashion. The adjuster shaft 5b is operatively connected to the driver shaft 5'b of a driver device via the synchronization device 11, which will be described further below.

In the other spindle unit 5', the driver device is arranged with the driver shaft 5'b coaxially with respect to the other spindle unit 5', with respect to the threaded ram 6' thereof and the driver axis 5'a. In the brake-application-side end region of the driver shaft 5'b, a synchronization wheel 11'a of the synchronization device 11 is attached in a rotationally fixed fashion, as in the case of the adjuster shaft 5b. The brake-application-side end of the driver shaft 5'b is coupled here to a wear sensor 12 which is arranged in a hood-shaped housing over the brake-application-side end of the driver shaft 5'b on the brake caliper 4. The wear sensor 12 is coupled in a rotationally fixed fashion to the threaded ram 6' via the driver shaft 5b. A pick-up element of the wear sensor can be, for example, an angle sensor, for example a potentiometer. It detects the angular position of the threaded ram 6' about the driver axis 5'a. The evaluation of this angular position permits a conclusion to be made about the state of wear of the brake pads 3 and of the brake disc 2 because the threaded ram 6' is coupled to the threaded ram 6 via the driver shaft 5'b and therefore by means of the synchronization device 11 (explained in more detail below). The wear sensor 12 therefore serves to detect adjustment travel, i.e. the wear state, and is connected here (in an electrically conductive or optically transmissive fashion) to a brake control unit 19 via a connecting line 13a which is provided with a plug-type connector 13, said brake control unit being able to perform, inter alia, the evaluation of the measured value which is detected by the wear sensor 12.

In addition, the wear sensor 12 is also connected to a control device 20a of the clearance-monitoring device 20. This will also be explained in detail below.

Customary pneumatic disc brakes 1 such as are described, for example, in DE 197 29 024 C1 have the adjustment device 10 together with the driver device as integrated, automatically operating wear adjustment devices. Through mechanical adjustment of the position of the threaded spindles 6, 6' in the crossmember 7, preceding wear of the friction-partner brake pads 3 and the brake disc 2 is compensated and as a result the previously defined clearance is maintained.

Drive is provided for the adjustment movement of the adjustment device 10 by means of a secondary function of the brake lever 8 with an output finger 8*a* (or a plurality thereof). The brake lever 8 is, as already mentioned above, activated, for example, by a brake cylinder (pneumatically, hydraulically or electrically).

The adjustment device 10 therefore interacts with the brake lever 8 via a drive 9. The drive 9 comprises an activator which is embodied as a drive finger 8*a* which is connected to the brake lever 8, and a shift fork finger 10*b* of the drive element 10*a* of the adjustment device 10. The drive 9 will be described in more detail below with respect to FIGS. 3 and 4.

When the adjustment device 10 is driven by the drive 9 by means of the brake lever 8, for example a one-way coupling of the adjustment device 10 is activated, said adjustment device 10 being coupled to the adjuster shaft 5*b* via a friction clutch, for example. A detailed description of the function of the adjustment device 10 can be found in document DE 10 2004 037 771 A1.

The adjustment movement of the one threaded ram 6, which is also a rotational movement or pivoting movement of the adjuster shaft 5*b*, is transmitted by way of the synchronization device 11 to the driver shaft 5'*b* and therefore to the other threaded ram 6'. For this purpose, the adjuster shaft 5*b* of the adjustment device 10 and the driver shaft 5'*b* of the driver device are coupled by the synchronization device 11 in such a way that a rotational movement of the threaded ram 6 about the adjuster axis 5*a* brings about a corresponding rotational movement of the threaded ram 6' about the driver axis 5'*a*, and vice versa. In the example illustrated in FIG. 1, the synchronization device 11 is arranged at the brake-application-side ends of the adjuster shaft 5*b* and of the driver shaft 5'*b*. In the variant according to FIG. 2, the synchronization device 11 is located on the brake-application side of the crossmember 7. The synchronization device 11 comprises the synchronization wheel 11*a* which is coupled to the threaded ram 6 of the one spindle unit 5 and to the adjuster shaft 5*b* of the adjustment device 10, the other synchronization wheel 11'*a* which is coupled to the threaded ram 6' of the other spindle unit 5' and to the driver shaft 5'*b* of the driver device, and a synchronization mechanism 11*b* to which the synchronization wheels 11*a* and 11'*a* are coupled. In this exemplary embodiment, the synchronization mechanism 11*b* is a traction device, in the present example a chain. The synchronization wheels 11*a*, 11'*a* are therefore embodied as chain wheels. This ensures synchronous movement of the threaded rams 6, 6' of the spindle units 5 and 5' during wear adjustment processes (driven by the adjuster shaft 5*b* of the adjustment device 10) and setting operations during maintenance work, for example changing of pads, (manual drive, for example via an activation end of the adjuster shaft 5*b* of the adjustment device 10, which is not illustrated but can easily be imagined).

Figure 3:
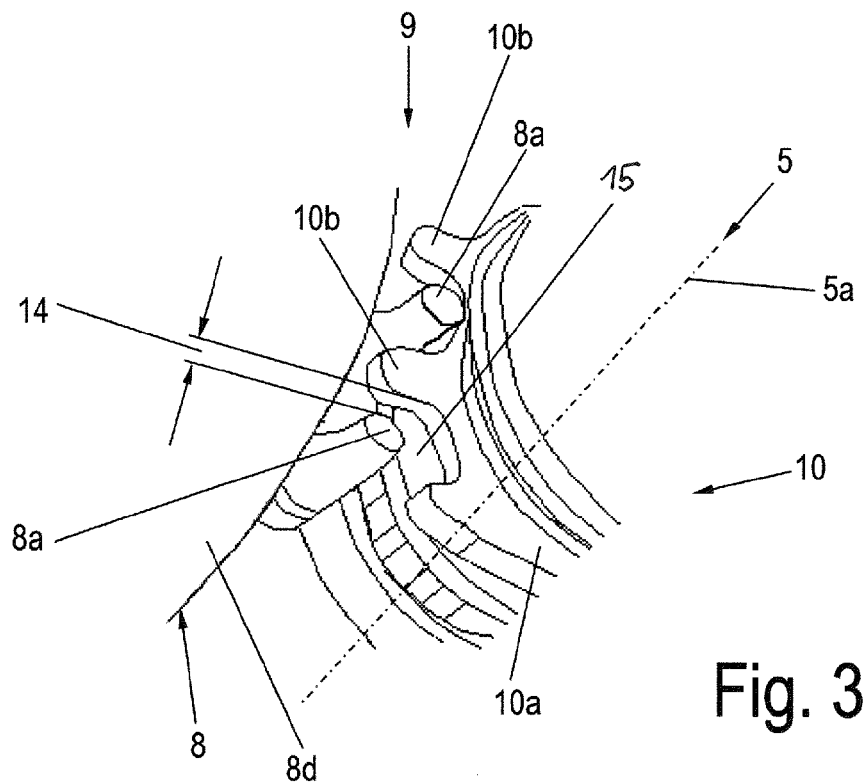
FIG. 3 shows an enlarged partial-perspective view of a drive of an adjustment device of the exemplary embodiment according to FIG. 1.
Figure 4:
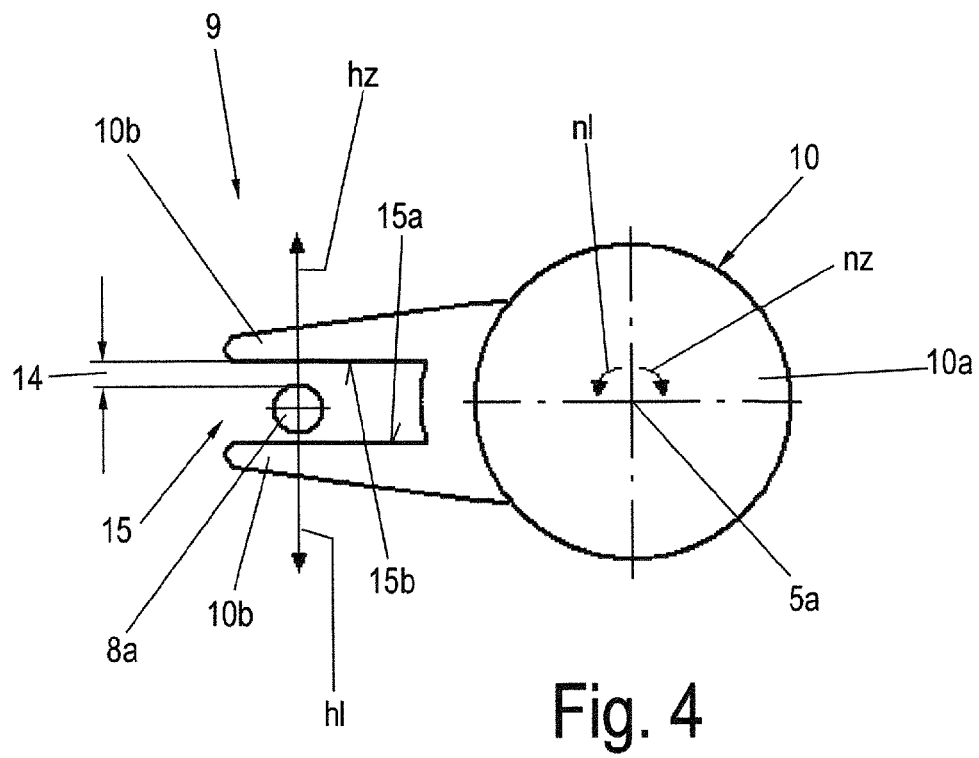
FIG. 4 shows a schematic plan view of the drive.

FIG. 3 illustrates an enlarged partial-perspective view of the drive 9 of the adjustment device 10 of the exemplary embodiment according to FIG. 1. FIG. 4 shows in this respect a schematic plan view of the drive 9.

On the left-hand side in FIG. 3, the lever body 8*d* of the brake lever 8 is indicated only schematically, while on the right-hand side the adjustment device 10 with the adjuster axis 5*a* of the one spindle unit 5 is shown partially. Two output fingers 8*a* in the form of pins or rods, which engage here with three shift fork fingers 10*b* of the drive element 10*a* of the adjustment device 10, are attached to the lever body 8*d*, wherein the output fingers 8*a* are each arranged here in a gap 15 between two shift fork fingers 10*b*. FIG. 4 shows a plan view of the arrangement of an output finger 8*a* in the gap 15 between two shift fork fingers 10*b*.

The brake lever axis 8*a* about which the brake lever 8 can pivot runs at a right angle to the adjuster axis 5*a* (see also FIG. 2). A pivoting movement of the brake lever 8 then brings about a pivoting movement of the output fingers 8*a*, which in FIG. 4 is in an upward direction (indicated by an arrow brake application hz) or downward (indicated by an arrow release h1), wherein this pivoting movement is transmitted to the shift fork fingers 10*b* and therefore to the drive element 10*a* of the adjustment device 10.

In the unactivated position, i.e. in the release position, as shown in FIGS. 3 and 4, play or idle travel 14 is provided between an activation contour of the output finger 8*a* and a shift fork wall 15*b* of the shift fork finger 10*b* of the drive element 10*a* of the adjustment device 10. This idle travel represents the structural clearance of the disc brake 1, taking into account the transmission ratios at the brake lever 8. In other words, activation of the adjustment device 10 does not take place until after the crossmember 7 has been shifted toward the disc brake 2 by a larger distance than the structural clearance by a pivoting movement of the brake lever 8 during a brake-application operation of the disc brake 1, i.e. when the brake is activated.

Irrespective of the particular structural embodiment of the adjustment device 10, which is indicated here only by way of example, the structurally defined clearance is always determined here by the idle travel 14 in the kinematic chain between the brake lever 8 and the one-way coupling of the adjustment device 10, wherein the one-way coupling is connected to the drive element 10*a*. When a brake application operation occurs, this idle travel 14 is firstly passed through in the direction of brake application hz, wherein there is no transmission of movement to the adjustment device 10 via the shift fork fingers 10*b*. In this context, there is also no adjustment, as a result of which the minimal clearance of the disc brake 1 is ensured. That is to say the idle travel 14 in the activation mechanism is directly proportional to the clearance.

As soon as the output finger 8*a* touches the shift fork wall 15*b*, the movement is transmitted to the shift fork finger 10*b* on the basis of the engagement with the output finger 8*a*, which results in a pivoting movement nz in the clockwise direction of the drive element 10*a* of the adjustment device 10. This pivoting movement is transmitted by the one-way coupling, coupled to the drive element 10*a*, to the adjuster shaft 5*b*, wherein the clearance is reduced.

When the disc brake 1 is released, the brake lever 8 is pivoted back, wherein the output finger 8*a* is moved in the direction of release h1. In this context, it comes into contact with the other shift fork wall 15*a* and therefore pivots the drive element 10*a* in a pivoting movement n1 in the counterclockwise direction. Since the drive element 10*a* is coupled to the one-way coupling of the adjustment device 10, this movement is not transmitted to the adjuster shaft 5*b* (this would then be an enlargement of the clearance, which is not desired).

The adjustment movement for reducing the clearance, which movement is carried out by the adjuster shaft 5*b*, is transmitted, as described above, to the driver shaft 5'*b* and also to the wear sensor 12, via the synchronization device 11. The wear sensor 12 generates, as a function of the angular position of the driver shaft 5'*b*, an electrical signal (analog or digital) which is proportional to the angular position and is evaluated in an electric/electronic device, for example in the brake control unit 19, as a measure of the wear of the brake pads 3 and also of the brake disc 2 of the disc brake 1 for the continuous detection of the wear of the friction partners (brake pads 3 and brake disc 2). The adjustment (extension, adjustment), which progresses with the wear, of the threaded spindles 6, 6' can therefore be detected by measuring technology. This electric/electronic device is based, for example, on a potentiometer measurement of the adjustment travel, i.e. of the rotational angle, of the threaded spindles 6, 6', which is integrated in each wheel brake of an associated vehicle. The measured values are monitored in a wheel-specific fashion in an evaluation unit, and when a predefined wear value or limiting value (corresponding to the extended or adjusted state of the threaded spindles 6, 6') is reached, a message, for example an acoustic and/or visual warning signal, is issued.

With the clearance-monitoring device 20 according to the invention, unacceptable deviations of the clearance of previously defined values are detected and displayed. The device 20 comprises a control device 20*a* (FIG. 1) which is described in more detail below. The control device 20*a* is coupled to the wear sensor 12 and the brake control unit 19. In this context, the control device 20*a* uses signals of the wear sensor 12 and of the brake control unit 19.

Firstly, a relationship between a brake-application force, the clearance, an adjustment and the wear sensor 12 will be described.

Figure 5:
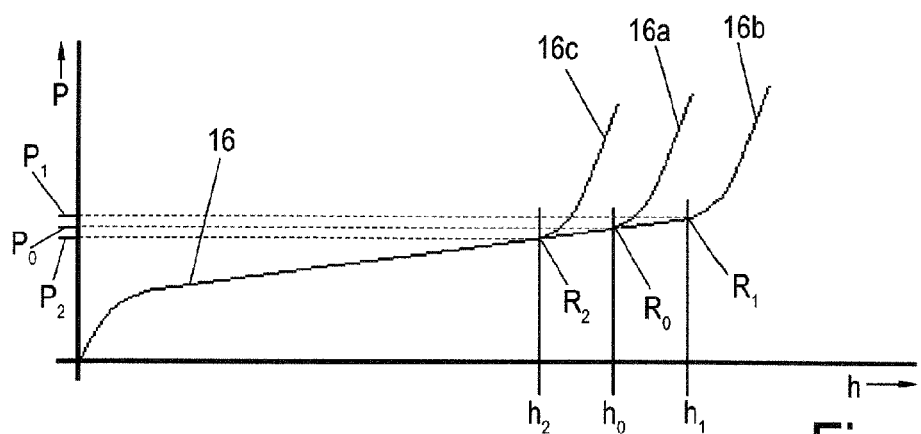
FIG. 5 shows a schematic diagram of a pressure-travel characteristic curve.
Figure 5A:
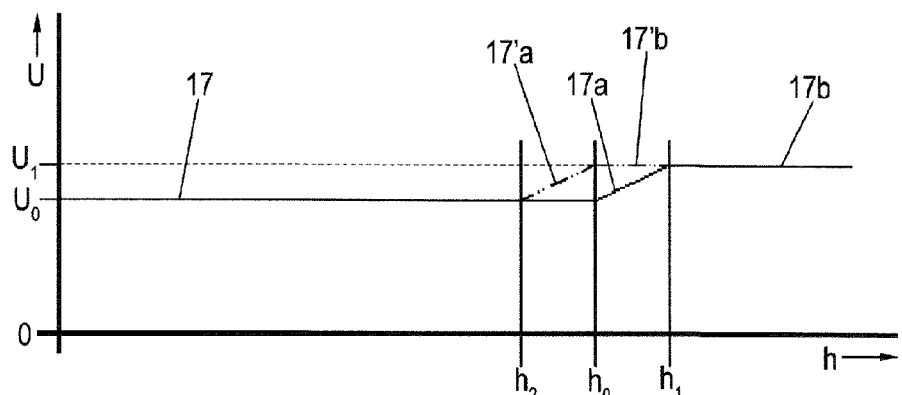
FIG. 5a shows a schematic diagram of a sensor signal.

FIG. 5 shows in this respect a schematic diagram of a pressure-travel characteristic curve. FIG. 5*a* shows in this respect a schematic diagram of a sensor signal.

In the schematic diagram in FIG. 5, a brake pressure p of the brake-application device of the disc brake 1 is represented on an ordinate plotted against a lever travel h (abscissa). The brake pressure p can be, for example, the air pressure of a pneumatic cylinder and/or hydraulic cylinder or the brake-application force of a brake activation powered by electric motor. The lever travel h is to be understood as meaning travel of the brake lever 8.

FIG. 5*a* shows with the same abscissa the lever travel h as illustrated in FIG. 5. However, a signal value U of a sensor signal 17 of the wear sensor 12 is plotted against the lever travel h here. In this example it is assumed that the wear sensor 12 has a potentiometer as a pick-up element, i.e. an electrical resistance which can vary as a result of the pivoting movement, described above, of the driver shaft 5'*b* and to which a constant electrical voltage is applied. In this example, the signal value U is then an electrical voltage which can be tapped at the pick-up element and to which pivoting of the driver shaft 5'*b* is proportional. That is to say the signal value U is, as an electrical voltage, proportional to adjustment of the adjustment device 10. The signal value U changes only when adjustment occurs.

The curve of an exemplary pressure-(force-)travel characteristic curve of a brake, for example the disc brake 1, is indicated with the reference symbol 16 in FIG. 5. The brake cylinder interacts with the brake lever 8.

Activation of the brake-application device comprises brake application and release. In the unactivated state (brake pressure=0), the brake cylinder and the brake lever 8 are in the initial position or released position shown in FIGS. 1, 2, by means of the internal return spring 7*a*. When the brake pressure p or the brake cylinder force output increases, for example a piston rod (not shown) moves the brake lever 8 through interaction with the force-application section 8*c* (FIG. 2), and said brake lever 8 moves the brake-application elements (crossmember 7 with the threaded spindles 6, 6') in the brake caliper 4. As soon as the structural clearance, which is also referred to as nominal clearance, is overcome (idle travel 14 in FIGS. 3 and 4), the output finger 8*a* of the brake lever 8 makes contact with the shift fork finger 10*b* of the drive element 10*a* with the one-way coupling of the adjustment device 10. This is the case with a lever travel $h_0$.

When the brake-application operation occurs, the brake pressure p increases in the region of spanning the clearance up to the lever travel $h_0$ with a relatively small gradient of the curve 16. In this region, the clearance is spanned. The clearance therefore corresponds to the lever travel h from the zero point up to the lever travel $h_0$. At a friction point $R_0$, the curve 16 of the brake pressure p intercepts a parallel to the ordinate, which runs through the lever travel $h_0$. In the case of the lever travel $h_0$, a brake pressure $p_0$ is assigned to the curve 16.

The term "friction point" is the point at which the brake pads 3 bear against the brake disc 2 of the disc brake 1. A further brake-application operation (brake-application section 16*a*) then brings about a braking process or braking through pressing of the brake pads 3 with increasing force against the brake disc 2, wherein the brake pressure p increases strongly in a brake-application section 16*a*. Release of the brake-application device (by reducing the brake pressure p) brings about a reversal of the process described above.

Figure 6:
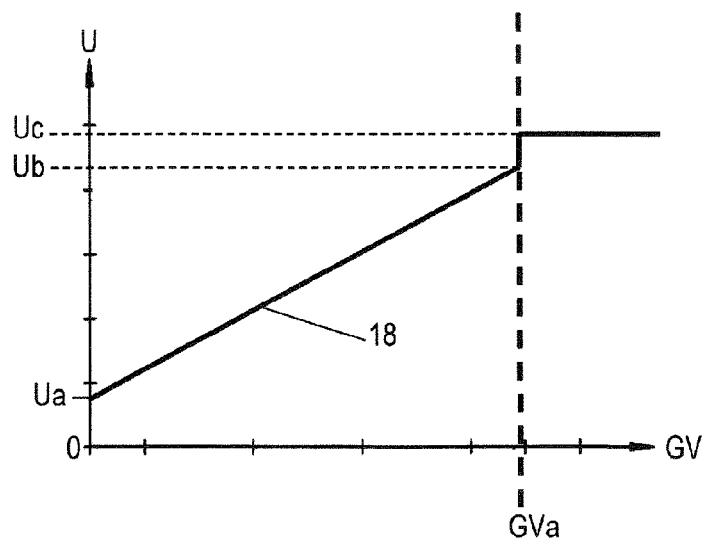
FIG. 6 shows a schematic diagram of a sensor characteristic curve.

FIG. 6 shows a schematic diagram of a sensor characteristic curve 18. In this context, a signal value U, for example an electrical voltage, is plotted on the ordinate against a total wear GV on the abscissa. The total wear GV relates to the friction partners of the brake pads 3 and the brake disc 2. In the case of new friction partners there is not yet any wear present and an output value is specified as a signal value Ua. The sensor characteristic curve 18 is linear here and extends with a specific gradient from the output value Ua to a final value Ub, to which a total wear GVa is assigned. In the case of the total wear GVa, it is necessary to replace at least the brake pads 3, and a wear limit has been reached. This is specified by a voltage jump to the signal value Uc, with respect to which the wear sensor 12 is correspondingly designed. The signal value Ua has, as an output value, for example a voltage of approximately 0.8V. The total wear GVa is reached in the case of a voltage of approximately 3.5 V at the signal value Ub. There is then a voltage jump to the signal value Uc, which is approximately 4 V. Of course, other voltage values or else current values (or else other values) can also be used as signal values U.

A differentiation of cases is performed. Firstly, the case in which a current friction point corresponds to a setpoint friction point is considered. Here, according to FIG. 5 the friction point $R_0$ coincides with the lever travel $h_0$, and there is no adjustment by the adjustment device 1. This occurs if, for example, the brake pads 3 are new or adjustment has taken place during a previous braking process. This means that a current clearance corresponds to the previously defined clearance, and adjustment is not necessary. Adjustment is therefore not carried out. The brake pads 3 already bear against the brake disc 2, and the brake pressure p increases strongly in the brake section 16a.

In this respect FIG. 5a shows the associated sensor signal 17 which is constant in the state of rest of the disc brake 1, that is to say when the brake-application device is not activated, and when activation occurs up to the overcoming of the structural clearance up to the point when the lever travel $h_0$ is reached. This is specified in FIG. 5a by the signal value $U_0$. The signal value $U_0$ therefore corresponds to an adjustment value which originates from an adjustment which was the last to take place, or forms an output value in the case of new brake pads 3.

Although a proceeding movement of the output finger 8a in the case of increasing brake pressure p in the brake section 16a is transmitted to the shift fork finger 10b of the drive element 10a of the adjustment device 10 (FIGS. 3, 4), an overload coupling which is present in the adjustment device 10 is triggered, since the brake pads 3 already bear against the brake disc 2. The drive element 10a then carries out a relative movement with respect to the fixed adjuster shaft 5b. Therefore, no adjustment takes place. The adjuster shaft 5b and the driver shaft 5'b which is coupled to it via the synchronization device 11, with the wear sensor 12 coupled to said driver shaft 5'b, are not adjusted.

The sensor signal 17 is therefore not changed and remains constant at the signal value $U_0$.

In addition, FIG. 5 also shows the cases in which the current friction point does not correspond to the setpoint friction point in the case of the lever travel $h_0$. Firstly, the case is considered in which the clearance owing to the wear of the brake pads 3 has become greater as a result of preceding braking processes. That is to say the current friction point has shifted to a larger value of the lever positioning travel h. This current friction point is specified here as a friction point R1 in the case of a lever travel $h_1$. The lever travel $h_1$ is larger here than the preceding lever travel $h_0$, which is caused by the fact that owing to the wear of the brake pads 3 a larger clearance has to be spanned, specifically the structural clearance up to the lever travel $h_0$, and subsequent thereto the clearance caused by the wear, up to the lever travel $h_1$. When this friction point $R_1$ is reached with the assigned brake pressure $p_1$, the brake pressure p increases strongly in a brake-application section 16b which has moved to the right in FIG. 5.

However, when the lever travel $h_0$ with the assigned brake pressure $p_0$ is reached, the current friction point $R_1$ is not yet reached. The adjustment device 10 is then activated, since the brake pads 3 do not yet bear against the brake disc 2, and the overload coupling of the adjustment device 10 is not triggered. The proceeding movement of the output finger 8a when the brake pressure $p>p_0$ increases is transmitted again to the shift fork finger 10b of the drive element 10a of the adjustment device 10 (FIGS. 3, 4). The drive element 10a then pivots the adjuster shaft 5b by means of the one-way coupling. Adjustment therefore takes place. The adjuster shaft 5b and the driver shaft 5'b, which is coupled to it by means of the synchronization device 11, with the wear sensor 12 coupled to said driver shaft 5'b, are adjusted. This is indicated in FIG. 5a by an adjustment signal section 17a of the sensor signal 17, which slopes upward with a specific gradient.

In this case, the signal value $U_0$, which is assigned to the lever value $h_0$ changes to the new signal value $U_1$ at the lever value $h_1$. In the example shown, $U_1$ is greater than $U_0$, but the inverse can, of course, also be possible in a different embodiment. After the adjustment to the previously defined clearance has been carried out in the friction point $R_1$, the signal value $U_1$ then corresponds to the current wear of the brake pads 3 and the brake disc 2. This signal value $U_1$ remains constant up to a change as a result of a subsequent adjustment. This is shown by a constant signal section 17b starting from the lever value $h_1$ in FIG. 5a.

In the other case, the drive element 10a of the adjustment device 10 may have carried out, with its shift fork finger 10b (FIGS. 3, 4), for example owing to a fault, a rotational movement (in FIG. 4 in the pivoting movement n1 counter to the clockwise direction) in opposition to its functionally defined rotational direction of the pivoting movement nz (that is to say counter to the locking direction of the one-way coupling which is coupled to the drive element 10a). The required idle travel 14 in the adjustment process is therefore reduced. This results, during the next braking operation, in a friction point $R_2$ at the lever travel $h_2$, wherein the lever travel $h_2$ is shorter than the lever travel $h_0$. In this context, braking (brake section 16c) already takes place before the structural clearance is reached at the brake pressure $p_0$ and lever travel $h_0$. After further braking operations, wear occurs to which adjustment then takes place at the friction point $R_2$ in the way described above. Undesired reduced clearance is generated by this correspondingly premature adjustment.

Likewise, the wear sensor 12 is correspondingly pivoted earlier when the earlier contact of the shift fork finger 10b with the output finger 8a (FIGS. 3, 4) occurs in the case of the lever travel $h_2$, and said wear sensor 12 now already changes the signal value $U_0$, in the case of the shorter lever travel $h_2$ in a signal section 17'a, to the constant signal section 17'b, which now already occurs in the case of the lever travel $h_0$. This is clarified in FIG. 5a with dash-double pointed lines for 17'a and 17'b.

In the brake control unit 19 (for example an electronic brake system EBS), the brake pressure values $p_0$, $p_1$, $p_2$ (and of course also other brake pressure values) which have been applied to the brake cylinder at the respective lever values $h_0$, $h_1$, $h_2$, are available. This results from the pressure-travel characteristic curve for the brake cylinder, which pressure-travel characteristic curve is stored in the brake control unit 19 as a reference value and/or in a memory unit 21 of the clearance-monitoring device 20 (see FIG. 7). A simplified similar characteristic curve 16 is shown in FIG. 5. There is therefore in each case a value pair p/u composed of the brake pressure p and a sensor response signal of the sensor signal 17 of the wear sensor 12. The term "sensor response signal" is to be understood as meaning the signal value U of the sensor signal 17 of the wear signal 12 including the chronological behavior of the signal value U. This will be explained below.

In this context, the abovementioned three cases are to be differentiated as follows.

In the first case, in which no adjustment occurs when the friction point $R_0$ is reached with the brake pressure $p_0$ and in the case of the lever travel $h_0$, the value pair p/u is composed of the brake pressure $p_0$ and the previously constant signal value $U_0$ of the wear sensor 12 because the current clearance corresponds to the nominal clearance. The sensor response signal is the constant signal value $U_0$ in this case.

In the second case, wear is present and the current friction point $R_1$ with the associated brake pressure $p_1$ is not reached until after the nominal clearance is spanned after the brake pressure $p_0$ has been passed through, without the brake section 16a being passed through and without a strong rise in the brake pressure p.

However, adjustment takes place here which starts at the brake pressure $p_0$ with the lever travel $h_0$ and results in a change in the signal value U of the sensor signal 17 of the wear sensor 12. In this case, this change in the signal value U of the sensor signal 17 is the sensor response signal. The assigned value pair p/u here has the brake pressure $p_1$ and the sensor response value $U > U_0$.

In the third case, with the brake pressure $p_2$ at the friction point $R_2$ in the case of the lever travel $h_2$, the nominal clearance (in the case of the brake pressure $p_0$ at the friction point $R_0$ in the case of the lever travel $h_0$) is undershot, wherein the brake pressure $p_2$ is accordingly smaller at the start of the change of the signal value $U_0$ of the sensor signal 17 of the wear sensor 12 than the nominal brake pressure $p_0$ (bearing pressure). The assigned value pair p/u has the brake pressure $p_2$ and the sensor response value $U < U_0$ here.

By comparing these values it is possible to determine whether the sensor response signal of the signal value U of the sensor signal 17 of the wear sensor 12 appears before, during or after the point when the corresponding nominal brake pressure $p_0$ is reached as the bearing pressure.

This difference between the nominal brake pressure $p_0$ (bearing pressure) and the current brake pressure p when the sensor response signal occurs before the nominal brake pressure $p_0$ is reached can be used as a basis for a trigger for the setting of a warning signal or of another measure.

Figure 7:
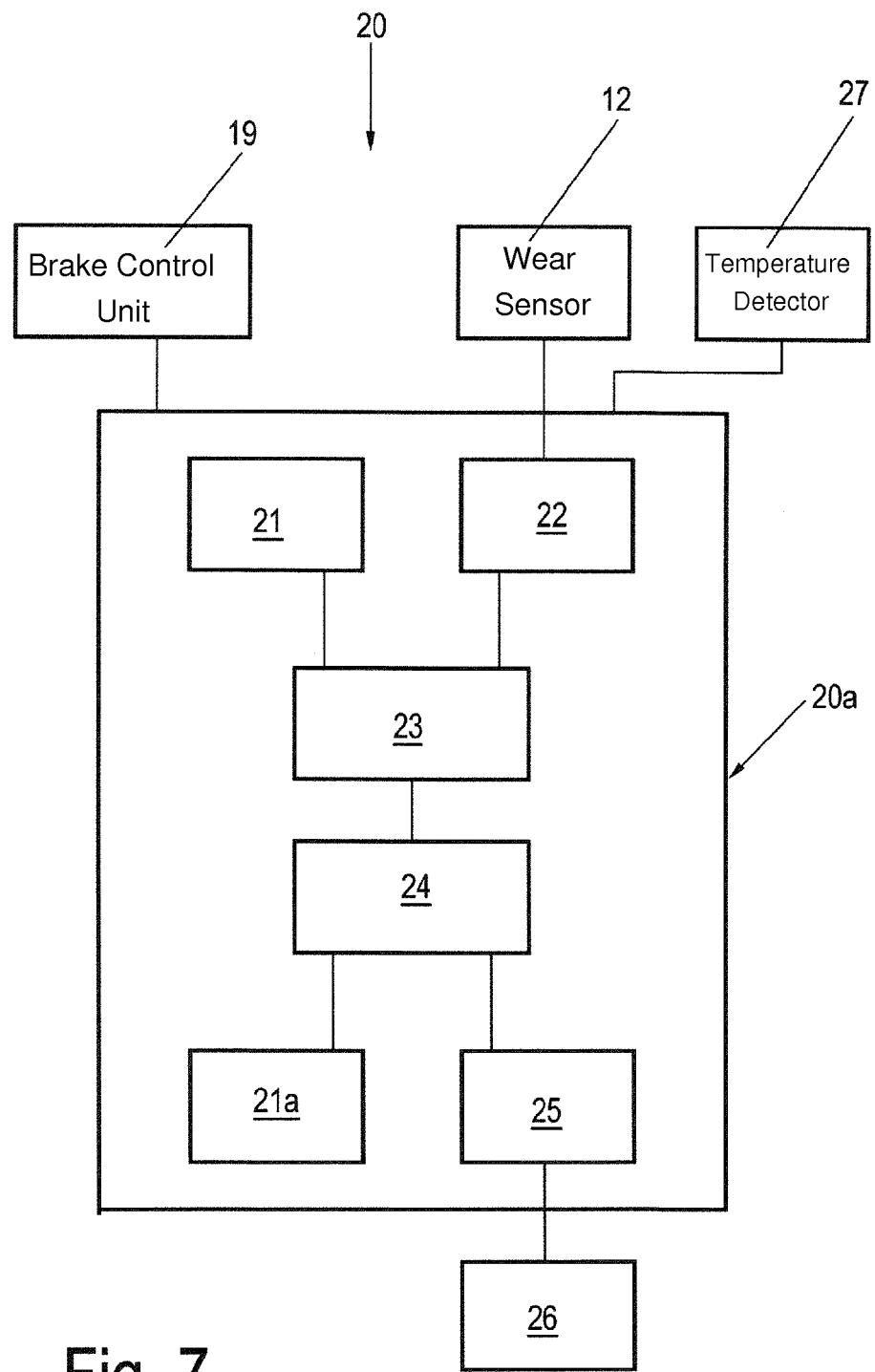
FIG. 7 shows a schematic block circuit diagram of a clearance-monitoring device.

Such monitoring of the clearance is performed with the clearance-monitoring device 20. In this respect, FIG. 7 shows a schematic block circuit diagram of the clearance-monitoring device 20.

On a vehicle, the clearance-monitoring device 20 is provided for each wheel brake, for example for six wheel brakes in the case of a three-axle commercial vehicle.

The clearance-monitoring device 20 comprises in this example the control device 20a, the wear sensor 12 and a signaling unit 26. Moreover, the brake control unit 19 is assigned to said clearance-monitoring device 20 in this exemplary embodiment, the control device 20a being connected to said brake control unit 19. Instead of the brake control unit 19, or in addition thereto, it is, of course, also possible to connect corresponding sensors to the control device 20a. These sensors may be, for example, a brake pedal sensor for detecting braking, a pressure sensor and/or force sensor for detecting the brake-application force or the brake pressure p, a lever travel sensor or brake cylinder piston-travel sensor for detecting the lever travel h. Moreover, the characteristic curve of the brake cylinder and/or of the disc brake 1 is stored as a pressure-travel characteristic curve, such as for example the characteristic curve 16 in FIG. 5, in the brake control unit 19 or in a specific memory device, for example in the control device 20a.

A temperature-detector 27 is illustrated as an example for the detection of additional variables which can possibly be used by the control device 20a to evaluate measured values and derived variables. Said temperature-detector 27 can be, for example, a temperature sensor on each wheel brake of an assigned vehicle, which temperature sensor is correspondingly connected to the control device 20a.

The connections to the control device 20a can be electrical or optical transmission links, and wireless connections are, of course, also possible, for example from each wheel brake of a vehicle to a central signaling unit 26.

The control device 20a comprises in this example a memory unit 21, a detection unit 22, a comparator unit 23, an evaluation unit 24 and an output unit 25.

The memory unit 21 serves to store, inter alia, previously definable values, for example table values and/or characteristic curves of the respective brake cylinder and wear sensor 12. The pressure-travel characteristic curve of the respective brake cylinder can, however, also be written into the memory unit 21 by means of so-called independent learning. This may occur, for example, in the new state of the disc brake 1. The same also applies to the characteristic curves of the wear sensors 12. Of course, further values can also be stored as references, limiting values, etc. in the memory unit 21. The memory unit 21 is connected to the comparator unit 23.

The memory unit 21 serves also to store the signal values which are detected by the wear sensor 12, either by means of a direct connection (not shown) thereto or, for example, via the brake control unit 19.

The detection unit 22 is connected to the wear sensor 12. Said detection unit 22 detects the current signal value U of the sensor signal 17 of the wear sensor 12. Furthermore, the detection unit 22 is connected to the comparator unit 23 and makes available the detected signal value U in a corresponding form, for example as a digital signal, to the comparator unit 23.

The comparator unit 23 forms current value pairs p/U with current brake pressure values p from the brake control unit 19 or from other sensors (not shown) and with the current signal values U supplied by the detection unit 22. The comparator unit 23 compares said value pairs with the table values or characteristic curve values from the memory unit 21 and/or from the brake control unit 19. The comparator unit 23 supplies its comparison results to the evaluation unit 24 to which it is connected.

The evaluation unit 24 evaluates the results received from the comparator unit 23, wherein said evaluation unit 24 also accesses the memory unit 21 (which is not illustrated). Depending on the evaluation, the evaluation unit 24 activates the output unit 25 connected to it, by transferring to said output unit 25 values, warnings, and information with corresponding instructions for output. Furthermore, the evaluation unit 24 is connected to a further memory unit 21a in which, for example, the current signal value U can be stored temporarily or for further use. Of course, other values can also be saved and/or stored in the memory unit 21a.

The output unit 25 prepares the information received from the evaluation unit 24 for displaying or signaling and transmits said information in a suitable form to the signaling unit 26.

In the case of a braking process which is detected by the clearance-monitoring device 20 via the brake control unit 19 or, for example by means of a brake pedal sensor, the clearance-monitoring device 20 is activated.

The current value pairs p/U formed by the comparator unit 23 are compared with the value pairs stored in the memory unit 21. In the event of an increase in the brake pressure p it is monitored whether, up to the point when the nominal brake pressure $p_0$ is reached, there is a change in the constant signal value U of the wear sensor 12. If this is the case ($U > U_0$), the evaluation unit 24 issues a warning to the output unit 25 for the purpose of acoustic, visual, haptic and/or alphanumeric signaling by the signaling unit 26 that the nominal clearance is undershot.

If the nominal brake pressure $p_0$ is reached, a sensor response signal is not registered and the brake pressure p increases strongly according to the brake section 16a (stored in the memory unit 21), it is assumed that no adjustment occurs and the clearance is correct.

If the nominal brake pressure $p_0$ is reached, a sensor response signal is registered and the brake pressure p does not increase strongly but instead the stored characteristic curve 16 continues to run, the evaluation unit 24 informs the signaling unit 25 that an adjustment is taking place. In this case, an evaluation of the adjustment can also be carried out in such a way that the adjustment is small, normal or large.

The monitoring of the clearance is summarized in the following table.

TABLE 1

Differentiation of cases

| Value pair p/U | Clearance | Message |
|---|---|---|
| $p = p_0$ and $U = U_0$ | Correct | Clearance correct |
| $p > p_0$ and $U > U_0$ | Too large | Adjustment |
| $p < p_0$ and $U < U_0$ | Undershot | Warning |

Figure 8:
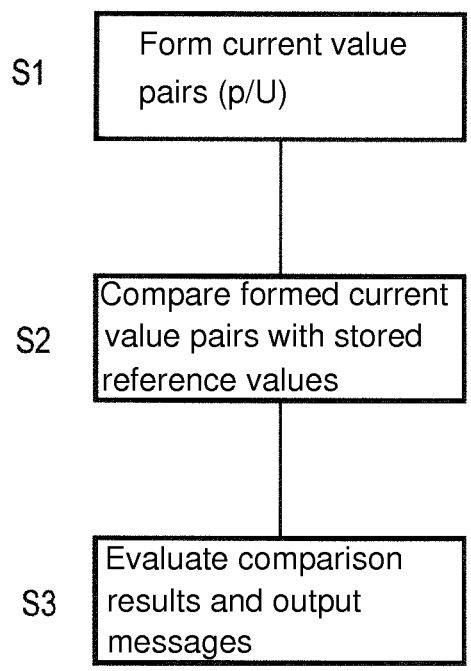
FIG. 8 shows a flowchart of an exemplary embodiment of a method according to the invention.

FIG. 8 shows a flowchart of an exemplary embodiment of a method according to the invention for monitoring clearance with the clearance-monitoring device described above.

In this context, in a first method step S1 the current value pairs p/U are formed during a braking process, wherein the signal values U are detected.

In a second method step S2, the current value pairs p/U are compared with the value pairs stored in the memory unit 21.

And on the basis of these comparisons, evaluation with possible signaling takes place in a third method step S3.

Under certain operating states of the disc brake 1 it may be expedient to avoid an excessively early or unnecessary warning signal. If, for example, the clearance is reduced only temporarily by thermal influences ($p<p_0$ and $U<U_0$) and normalizes again after cooling, a warning is not necessary. For this purpose, the control device 20a can be connected to a temperature-detector 27. The temperature-detector 27 can be, for example, a separate temperature sensor on the disc brake 1, or a temperature value which is supplied by the brake control unit 19.

In accordance with the characteristics of the disc brake 1 and friction partners it is possible to develop various strategies for the evaluation of the data (value pairs p/U; temperature) by means of the evaluation unit 24. It is therefore possible, for example, for the outputting of a warning or of a warning signal to be defined only, for example, after a specific number of measured values or monitoring processes (current value pairs p/U) outside the tolerance. A specific trend of the measured values in the current value pairs p/U can also be used as the basis for a message (positive, negative or neutral).

While the detection and evaluation of the value pairs p/U can take place at any desired operating time of the disc brake 1 by means of the clearance-monitoring device 20, various procedures are, of course, possible. Both the time and the frequency of the clearance monitoring can be defined as a function of the type or use of the vehicle. It is therefore possible, for example, to carry out the clearance monitoring in the stationary state of the vehicle (by initiating automatic application of the brake or by means of the signaling unit with a request to the driver) or while driving. It is also possible for clearance monitoring to take place only after a specific number of braking operations, or continuously.

The assignment described above (value pairs p/U), brake pressure (bearing pressure) p and sensor response signal as the signal value U of the wear sensor 12 can be derived from the pressure-travel characteristic curve of the brake cylinder which is used and the known geometric values of the disc brake 1. For more precise and specific detection of the corresponding data of a vehicle brake (brake caliper 4 with brake cylinder) it is possible, for example in the new state of the disc brake 1, to learn the response pressure in the system or the clearance-monitoring device 20. In this context, in the case of a controlled pressure increase of the brake pressure p in the brake cylinder the signal value U of the wear sensor 12 is monitored, and the pressure p at the response time or the total characteristic curve is stored.

Further characteristic variables of the disc brake 1, whose consideration for the measuring accuracy for clearance monitoring is advantageous, can also be learned and included in the evaluation of the measured values. Since the wear sensor 12 is usually moved by means of mechanical transmission elements (gearwheels, chain or the like) mechanical play processes influence the synchronous movement of the brake lever 8 and wear sensor 12, and therefore the sensor signal 17. The composite play of these mechanical play processes between the output finger 8a of the brake lever 8 and the wear sensor 12 brings about hysteresis in the voltage profile of the curve of the sensor signal 17 during the brake application (brake stroke) and release (return stroke). This hysteresis can be measured by measuring the signal values U of the sensor signal 17 during the ventilation and venting of the brake cylinder, and can be stored in the memory unit 21 and used to correct the measurement results.

The clearance-monitoring device 20 is described by way of example for a specific type of disc brake 1.

The invention is not restricted to the exemplary embodiments described above. It can be modified within the scope of the appended claims.

The clearance-monitoring device 20 can therefore also be used for other designs of the adjustment device 10, drive 9 and electronic wear sensor, since the functional principles also apply here.

The application in drum brakes is also possible since these are to a certain extent also equipped with electronic wear-detection mechanisms and control devices with brake control (EBS) and comply with the same rules in terms of the adjustment principle.

It is conceivable that the clearance-monitoring device 20 which is provided for each wheel brake is arranged at a central location on a vehicle, for example at or in the common brake control unit 19. The clearance-monitoring devices 20 can also be a component of a software of the brake control unit 19 here.

LIST OF REFERENCE SYMBOLS

1 Disc brake
2 Brake disc
2a Brake disc axis
3 Brake pad
3a Brake pad carrier
4 Brake caliper
5,5' Spindle unit
5a Adjuster axis
5'a Driver axis
5b Adjuster shaft
5'b Driver shaft
6,6' Threaded spindle
6a, 6'a Pressure element
7 Crossmember
7a Return spring
8 Brake lever
8a Output finger
8b Arm
8c Force-application section
8d Lever body
8e Brake lever axis
9 Drive 10 Adjustment device
10a Drive element
10b Shift fork finger
11 Synchronization device
11a,11'a Synchronization wheel
11b Synchronization mechanism
12 Wear sensor
13 Plug-type connector
13a Connecting line
14 Idle travel
15 Gap
15a,15b Shift fork wall
16 Curve
16a-c Brake section
17 Sensor signal
17a,17'a Adjustment signal section
17b,17'b Constant signal section
18 Sensor characteristic curve
19 Brake control unit
20 Clearance-monitoring device
20a Control device
21,21a Memory unit
22 Detection unit
23 Comparator unit
24 Evaluation unit
25 Output unit
26 Signaling unit
27 Temperature-detector
GV,GVa Total wear
$h, h_0, h_1, h_2$ Lever travel
h1 Release
hz Brake application
n1,nz Pivoting
$p, p_0, p_1, p_1$ Brake pressure
$R_0, R_1, R_2$ Friction point
S1-S3 Method step
$U, U_0, U_1, U_a-U_c$ Signal value The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A disc brake for use with a brake disc, brake pads being arranged in the disc brake, the disc brake comprising:
   a brake-application device having a brake lever;
   an adjustment device coupled to the brake-application device in order to adjust for wear of the brake pads and the brake disc;
   a wear sensor configured to detect a wear value of the brake pads and the brake disc;
   a brake control unit for the disc brake; and
   a clearance-monitoring device comprising a control device connected to the wear sensor, the brake control unit and at least one temperature sensor,
   wherein
   the clearance-monitoring device is configured to evaluate measured values from at least the wear sensor and the at least one temperature sensor, identify secondary conditions based on signals from the at least one temperature sensor, learn and estimate trends, and include characteristic variables of the disc brake in the evaluation of the measured values,
   the wear sensor includes a pick-up element in the form of a potentiometer whose electrical resistance is variable is response to rotation of a driver shaft of the adjustment device,
   the pick-up element is configured to generate a signal in the form of an electrical voltage which is proportional to the rotation of the driver shaft,
   the disc brake characteristic variables includes a brake pressure, and
   in the evaluation of the measured values, the clearance monitoring device is configured to issue signals indicative of a current clearance state based on comparison of a current brake pressure value and wear sensor information, where
   if the current brake pressure value equals a nominal brake pressure present when the brake pads contact the brake disc, and the pick-up device voltage signal equals a nominal voltage corresponding to a position of the pick-up device potentiometer when the brake pads contacted the brake disc in a preceding brake application, the clearance is evaluated as correct and a clearance correct signal is issued,
   if the current brake pressure value is greater than the nominal brake pressure, and the pick-up device voltage signal is greater than the nominal voltage, the clearance is evaluated as too large and a clearance adjustment signal is issued, and
   if the current brake pressure value is less than the nominal brake pressure, and the pick-up device voltage signal is less than the nominal voltage, the clearance is evaluated as undershot and a clearance warning signal is issued.

2. The disc brake according to claim 1, wherein the detection unit is configured to detect a change in the current signal value of the wear sensor over time.

3. The disc brake according to claim 1, wherein the current brake pressure values originate from the brake control unit and/or are output values of at least one other sensor.

4. The disc brake according to claim 1, wherein the stored reference values are stored in the brake control unit.

5. The disc brake according to claim 1, wherein the stored reference values are stored in a memory of the control device of the clearance-monitoring device.

6. The disc brake according to claim 1, wherein the control device of the clearance-monitoring device includes an evaluation unit that evaluates results of the comparator unit.

7. The disc brake according to claim 6, wherein the clearance-monitoring device further comprises a signaling unit, the signaling unit outputting the clearance signals about the state of the clearance at least one of acoustically, visually, haptically, and alphanumerically based on the evaluation of the evaluation unit.

8. The disc brake according to claim 1, wherein the control device of the clearance-monitoring device is a component of the brake control unit.

9. A method for monitoring a clearance of a disc brake having
   brake pads,
   a brake-application device having a brake lever,
   an adjustment device coupled to the brake-application device in order to adjust for wear of the brake pads and the brake disc,
   a wear sensor configured to detect a wear value of the brake pads and the brake disc, at least one temperature sensor,
a brake control unit, and
a clearance-monitoring device comprising a control device connected to the wear sensor, the brake control unit and at least one temperature sensor, and
the clearance monitoring device being configured to evaluate measured values from at least the wear sensor and the at least one temperature sensor, identify secondary conditions based on signals from the at least one temperature sensor, learn and estimate trends, and include characteristic variables of the disc brake in the evaluation of the measured values,
wherein the wear sensor includes a pick-up element in the form of a potentiometer whose electrical resistance is variable is response to rotation of a driver shaft of the adjustment device, the pick-up element is configured to generate a signal in the form of an electrical voltage which is proportional to the rotation of the driver shaft, and the disc brake characteristic variables includes a brake pressure,
the method comprising the acts of:
a) forming current value pairs from current brake pressure values and detected current signal values received by the control unit of the wear sensor during a braking process;
b) comparing the formed current value pairs with reference values previously stored at the control unit;
c) evaluating with the control unit the comparison in a manner that includes thermal influences based on signals from the at least one temperature sensor, and
d) determining from the comparison evaluation whether the clearance has changed and whether to output indicative of the clearance,
wherein in the comparing of the current value pairs, the clearance monitoring device is configured to issue signals indicative of a current clearance state based on comparison of a current brake pressure value and wear sensor information, where
the brake pressure pair includes the current brake pressure and a nominal brake pressure present when the brake pads contact the brake disc,
the pick-up device voltage pair includes the pick-up device voltage signal and a nominal voltage corresponding to a position of the pick-up device potentiometer when the brake pads contacted the brake disc in a preceding brake application,
if the current brake pressure equals the nominal brake pressure, and the pick-up device voltage signal equals the nominal voltage, the clearance is evaluated as correct and a clearance correct signal is issued,
if the current brake pressure value is greater than the nominal brake pressure, and the pick-up device voltage signal is greater than the nominal voltage, the clearance is evaluated as too large and a clearance adjustment signal is issued, and
if the current brake pressure value is less than the nominal brake pressure, and the pick-up device voltage signal is less than the nominal voltage, the clearance is evaluated as undershot and a clearance warning signal is issued.

10. The method according to claim 9, wherein in the method act (a) of forming current value pairs (p/U), the current brake pressure values (p) are supplied by the brake control unit and/or an additional sensor.

11. The method according to claim 9, wherein in the method act (c) of evaluating, a previously definable nominal clearance without adjustment is detected if a current value pair (p/U) corresponds to a stored value pair ($p_0/U_0$) which is assigned to a correct clearance, and the following value pair (p/U) does not have any change in the detected current signal value (U) of the wear sensor but does have a strong rise in the brake pressure (p).

12. The method according to claim 9, wherein in the method act (c) of evaluating, previously definable nominal clearance, enlarged owing to wear, with adjustment is detected if a current value pair (p/U) corresponds to a stored value pair ($p_0/U_0$) which is assigned to a correct clearance, and the following value pair (p/U) has a change in the detected current signal value (U) of the wear sensor but does not have a strong rise in the brake pressure (p).

13. The method according to claim 9, wherein in the method act (c) of evaluating, a previously definable nominal clearance is detected as being undershot if the brake pressure ($p_2$) of a current value pair (p/U) is lower than the brake pressure ($p_0$) which is assigned to a previously definable, correct clearance, and the subsequent value pair (p/U) does not have any change in the detected current signal value (U) of the wear sensor but does have a strong rise in the brake pressure (p) or has a change in the detected current signal value (U) of the wear sensor but does not have a strong rise in the brake pressure (p).

14. The method according to claim 9, wherein in the method act (c) of evaluating, a warning or a warning signal is not output until after a specific number of braking operations.

15. The method according to claim 9, wherein the reference values are stored in advance by learning in the brake control unit and/or the memory unit.

16. The method according to claim 9, wherein a friction point ($R_0$, $R_1$, $R_2$) is detected in that the current value pairs (p/U) are compared with stored value pairs if a current value pair (p/U) of the current value pairs (p/U) which are compared with stored value pairs has a strong rise in the brake pressure (p).

* * * * *